United States Patent [19]

Gastinger

[11] 4,448,897

[45] May 15, 1984

[54] METHOD FOR PRODUCING A VANADIUM-TITANIUM CATALYST EXHIBITING IMPROVED INTRINSIC SURFACE AREA

[75] Inventor: Robert G. Gastinger, Brookhaven, Pa.

[73] Assignee: Atlantic Richfield Company, Los Angeles, Calif.

[21] Appl. No.: 377,775

[22] Filed: May 13, 1982

[51] Int. Cl.$^3$ .......................... B01J 21/06; B01J 23/22
[52] U.S. Cl. ...................................... 502/350; 562/548
[58] Field of Search ............... 252/461; 562/547, 548; 502/350

[56] References Cited

U.S. PATENT DOCUMENTS 3,799,886  3/1974  Felice et al. .................. 252/461
3,954,857  5/1976  Brockhaus .................... 562/548

*Primary Examiner*—W. J. Shine
*Attorney, Agent, or Firm*—Dennis M. Kozak

[57] ABSTRACT

Mixed vanadium-titanium oxides catalysts having intrinsic surface areas before surface modification, greater than about 40 m$^2$/gram are disclosed. These catalysts are suitable for use in the preparation of acetic acid by gas-phase oxidation of butenes.

7 Claims, No Drawings

METHOD FOR PRODUCING A VANADIUM-TITANIUM CATALYST EXHIBITING IMPROVED INTRINSIC SURFACE AREA

This invention relates to mixed vanadium-titanium oxides catalysts.

More specifically, this invention pertains to a method for the manufacture of a mixed vanadium-titanium oxides catalyst which exhibits improved intrinsic surface area.

In one of its more specific aspects, this invention pertains to the use of the mixed vanadium-titanium oxides catalyst in the preparation of acetic acid by gas-phase oxidation of butenes.

Vanadium-titanium catalysts are well-known to be useful for the oxidation of hydrocarbons such as o-xylene, acenaphthene and butene. A general method for the preparation of vanadium-titanium catalysts as described, for example, in U.S. Pat. Nos. 3,464,930, 4,048,112 and 4,238,370, involves the impregnation of preformed titania with a solution of a vanadium salt followed by solvent removal and calcination. Often an inert support is employed. Another catalyst preparation method is described in U.S. Pat. No. 4,228,038 and comprises repeatedly treating titania with water and vanadium oxytrichloride until the desired vanadium content is reached. Yet another method of obtaining a more intimately mixed vanadium-titanium catalyst is described in U.S. Pat. No. 3,954,857 and involves the neutralization of a hydrochloric acid solution of vanadium pentoxide and titanium tetrachloride. The teachings of the above referred to U.S. Patents are incorporated herein by reference.

The above prior art methods of preparing titanium-vanadium catalysts are deficient in that their use results in catalysts having maximum intrinsic surface areas of less than about 32 $m^2/g$ before surface modification, such as, for example, acid treatment.

A method has now been found for preparing titanium-vanadium catalysts having intrinsic surface areas up to at least 220 $m^2/g$ before surface modification. Moreover, these high surface area catalysts have been employed in the vapor phase oxidation of butene-1 to acetic acid and, quite surprisingly, found to require lower reaction temperatures to achieve similar conversions and selectivities as compared to the lower surface area prior art catalysts.

According to this invention, there is provided a mixed vanadium-titanium oxides catalyst having an intrinsic surface area before surface modification, greater than about 40 $m^2/gram$ as measured by the Brunauer, Emmett and Teller (BET) method of determining surface area.

Also, according to this invention, there is provided a method for producing a mixed vanadium-titanium oxides catalyst which method comprises forming a precipitate by mixing at least one vanadyl alkoxide, at least one titanium alkoxide and an aqueous solution, and recovering and calcining the resulting precipitate.

According to this invention, there is also provided in a process for the production of acetic acid by the vapor phase oxidation of butenes with oxygen or an oxygen-containing gas, which process comprises carrying out the reaction in the presence of a catalyst, wherein the improvement comprises using a mixed vanadium-titanium oxides catalyst having an intrinsic surface area before surface modification, of greater than about 40 $m^2/gram$ as measured by the BET method.

In the method of this invention, use can be made of any vanadyl alkoxide having the general formula: VO(OR)$_3$, wherein each R represents a $C_1$ to $C_8$ branched or linear alkyl group, such as, for example, methyl, ethyl, ethyl hexyl, isopropyl, sec-butyl, and n-butyl. A preferred vanadyl alkoxide is vanadyl tri-n-butoxide.

In the practice of this invention, use can be made of any titanium alkoxide having the general formula: Ti(OR)$_4$ wherein R is as defined above.

In the method of this invention the atom ratio of vanadium to titanium in the mixture will be within the range of from about 1 to 100 to about 9 to 1. Preferably, the atom ratio of vanadium to titanium will be within the range of from about 1 to 10 to about 2 to 1.

The aqueous solution employed in the mixture serves as a hydrolysis medium and can be acidic, neutral or basic. Preferably the aqueous solution will be acidic. A 50% by weight acetic acid solution has been found particularly suitable for use. Since the aqueous solution serves as a hydrolysis medium, the amount of aqueous solution employed can vary so long as it is employed in an amount sufficient to result in the formation of a precipitate.

The precipitate formed by mixing the alkoxides and aqueous solution is recovered and dried using conventional methods such as described in U.S. Pat. No. 4,276,197. The resulting dry solid precipitate is then calcined in an air stream, typically at temperatures from about 200° to 400° C., preferably from about 250° to 350° C. and for a period of time within the range of from about 2 to 16 hours. The resulting catalyst is then in the form of powder and can be pelletized or formed into extrudate as desired using conventional equipment.

The following examples demonstrate the method of making a mixed vanadium-titanium oxides catalyst of this invention and the use of the catalyst in the vapor phase oxidation of butene-1 to acetic acid. All catalyst surface areas were determined using the BET method.

EXAMPLE I (Invention)

This Example demonstrates the preparation of a mixed vanadium-titanium oxides catalyst according to the method of this invention.

Vanadyl tri-n-butoxide (50.0 g) and tetra-n-butoxy-titanium (61.2 g) were mixed with 500 g of a 50 wt.% aqueous acetic acid solution with stirring. The mixture was heated for 3 hours at 55°–60° C. The mixture was then cooled, filtered and the solid precipitate washed with water. The precipitate was then dried in vacuum at 100° C. for 4 hours, then calcined at 300° C. for 10 hours in air. The surface area of the resulting catalyst was found to be 220 $m^2/g$ before acid treatment. A mixture of 10.2 g of the catalyst with 10 ml concentrated hydrochloric acid was stirred at room temperature for 10 minutes. The solid was collected by filtration, washed with water, dried then calcined in air at 300° C. for 1 hour. The resulting acid treated catalyst was pelletized and sieved to 8–14 mesh (Tyler Standard Sieve). The surface area of the treated catalyst was found to be 285 $m^2/g$.

EXAMPLE II (Prior Art)

This Example demonstrates the preparation of a vanadium-titanium catalyst using substantially the method of U.S. Pat. No. 3,954,857 (Example I). A solution of 238 ml of concentrated hydrochloric acid, 128 ml water, 50.0 g vanadium pentoxide and 104 g titanium tetrachloride was added to an ice cooled flask simultaneously with an 8% ammonium hydroxide solution at a rate at which the temperature of the resulting mixture remained below 50° C. and the pH was between 1–2. After the addition was complete, the mixture was cooled, filtered and the solid washed with water, dried then calcined at 400° C. for 12 hours in air. The surface area of the resulting catalyst was found to be 33 m²/g, before acid treatment. The resulting catalyst was washed with concentrated hydrochloric acid for 19 minutes at room temperature, then dried and calcined under nitrogen at 400° C. for 1 hour, then under air at 400° C. for 1 hour. The surface area of the acid treated catalyst was found to be 48 m²/g.

EXAMPLE III

In a stainless steel tubular reactor ($\frac{3}{8}"$ $\phi$D) was charged 3.75 g of the catalyst prepared according to the method of Example I (Invention) and diluted with 20.0 g of silicon carbide using gradient packing. At 152° C. and a contact time of 0.71 second (based on catalyst void space) a feed stream of 1.61 mol.% butene and 27 mol.% water in air was passed over the catalyst. Butene conversion was 47%. Acetic acid selectivity was 57.7%. Acetaldehyde and acetone selectivities were 6.7 and 1.3%, respectively. Other products included formic acid, carbon monoxide and carbon dioxide. Catalyst productivity was 0.050 gram acetic acid per gram catalyst per hour.

EXAMPLE IV

Over the catalyst prepared as described in Example III was passed a feed stream of 1.97% butene and 25 mol.% water in air at 157° C. with a contact time of 0.41 second. Butene conversion was 37%. Acetic acid selectivity was 52%. Acetaldehyde and acetone selectivities were 7.1 and 1.7%, respectively. Catalyst productivity was 0.069 g acetic acid per gram catalyst per hour.

EXAMPLE V

In a stainless steel tubular reactor 4.00 g of the catalyst prepared according to the method of Example II (Prior Art) was diluted with 35.5 g of zirconium silicate was charged using gradient packing. At 177° C. and a contact time of 0.54 second a feed stream of 1.54 mol.% butene and 29% water in air was passed over the catalyst. The butene conversion was 47% and acetic acid selectivity was 63.6%. Acetaldehyde and acetone selectivities were 3.9 and 0.5%, respectively. Catalyst productivity was 0.054 g acetic acid per gram catalyst per hour.

It is seen from the foregoing that this invention provides a mixed vanadium-titanium oxides catalyst which, in the absence of acid treatment, exhibits intrinsic surface areas of up to at least 220 m²/gram. Accordingly, the surface areas of the catalysts of this invention are significantly increased over the surface areas of the prior art catalysts. Moreover, the catalysts of this invention when employed to produce acetic acid, require lower reaction temperatures to achieve similar conversions and selectivities as compared to the lower surface area prior art catalysts.

It will be evident from the foregoing that various modifications can be made to this invention. Such, however are considered to be within the scope of the invention.

What is claimed is:

1. A method for producing a mixed vanadium-titanium oxides catalyst which method comprises forming a precipitate by the mixing of at least one vanadyl alkoxide, at least one titanium alkoxide in an aqueous solution, recovering, drying and calcining the resulting precipitate.

2. The method of claim 1 in which said vanadyl alkoxide and said titanium alkoxide have respectively the general formula: $VO(OR)_3$ and $Ti(OR)_4$, wherein each R represents a $C_1$ to $C_8$ branched or linear alkyl group.

3. The method of claim 1 in which the atom ratio of vanadium to titanium in the mixture is within the range of from about 1 to 100 to about 9 to 1.

4. The method of claim 1 in which the atom ratio of vanadium to titanium in the mixture is within the range of from about 1 to 10 to about 2 to 1.

5. The method of claim 1 in which the aqueous solution is acidic.

6. The method of claim 1 in which the aqueous solution is basic.

7. The method of claim 1 in which the aqueous solution is neutral.

* * * * *